US005352579A

United States Patent [19]
Milliman
[11] Patent Number: 5,352,579
[45] Date of Patent: Oct. 4, 1994
[54] NUCLEIC ACID PROBES TO HISTOPLASMA CAPSULATUM
[75] Inventor: Curt L. Milliman, St. Louis, Mo.

[73] Assignee: Gen Probe, Inc., San Diego, Calif.

[21] Appl. No.: 720,587

[22] Filed: Jun. 28, 1991

[51] Int. Cl.[5] .......................... C12Q 1/68; C07H 21/02; C12N 15/00

[52] U.S. Cl. .......................................... 435/6; 536/22.1; 536/23.74; 536/24.32; 935/78

[58] Field of Search ..................... 435/6; 536/27, 22.1, 536/23.74, 24.32; 935/78

[56] References Cited

PUBLICATIONS

E. J. Keath et . J. Clin. Microbiol. 27, 2369–2372 (1989).

P. G. Standard and L. Kaufman J. Clin. Microbiol. 3, 191–199 (1976).

*Primary Examiner*—Amelia Burgess Yarbrough

*Assistant Examiner*—Eggerton Campbell

*Attorney, Agent, or Firm*—Lyon & Lyon

[57] ABSTRACT

This invention discloses hybridization assay probes specific for *Histoplasma capsulatum* and no other fungi.

15 Claims, No Drawings

NUCLEIC ACID PROBES TO HISTOPLASMA CAPSULATUM

FIELD OF THE INVENTION

The inventions described and claimed herein relate to the design and construction of nucleic acid probes to *Histoplasma capsulatum* which are capable of detecting the organism in test samples of, e.g., sputum, urine, blood and tissue sections, food, soil and water.

BACKGROUND OF THE INVENTION

Two single strands of deoxyribo- ("DNA") or ribo- ("RNA") nucleic acid, formed from nucleotides (including the bases adenine (A), cytosine (C), thymidine (T), guanine (G), uracil (U), or inosine (I)), may associate ("hybridize") to form a double stranded structure in which the two strands are held together by hydrogen bonds between pairs of complementary bases. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs.

When a first single strand of nucleic acid contains sufficient continuous complementary bases to a second, and those two strands are brought together under conditions which will promote their hybridization, double stranded nucleic acid will result. Under appropriate conditions, DNA/DNA, RNA/DNA, or RNA/RNA hybrids may be formed.

A probe is generally a single stranded nucleic acid sequence which is complementary to some degree to a nucleic acid sequence sought to be detected ("target sequence"). It may be labelled with a detectable moiety such as a radioisotope, antigen or chemiluminescent moiety. A background description of the use of nucleic acid hybridization as a procedure for the detection of particular nucleic acid sequences is described by Kohne, U.S. Pat. No. 4,851,330, and Hogan et al., EPO Patent Application No. PCT/US87/03009, entitled "Nucleic Acid Probes for Detection and/or Quantitation of Non-Viral Organisms".

Hogan et al., supra, also describes methods for determining the presence of RNA-containing organisms in a sample which might contain such organisms. These methods require probes sufficiently complementary to hybridize to the ribosomal RNA (rRNA) of one or more non-viral organisms or groups of non-viral organisms. The mixture is then incubated under specified hybridization conditions, and assayed for hybridization of the probe and any test sample rRNA.

Hogan et al. also describes probes which detect only specifically targeted rRNA subunit subsequences in particular organisms or groups of organisms in a sample, even in the presence of many non-related organisms, or in the presence of the closest known phylogenetic neighbors. Specific examples of hybridization assay probes are provided for *Mycobacterium avium*, *Mycobacterium intracellulare*, *Mycobacterium tuberculosis*, *Mycobacterium africanum*, *Mycobacterium bovis*, *Mycobacterium microti*, the genus Mycobacterium, *Mycoplasma pneumoniae*, the genus Legionella, *Chlamydia trachomatis*, the genus Campylobacter, Enterococcus, the genus Pseudomonas group I, *Enterobacter cloacae*, *Proteus mirabilis*, the genus Salmonella, *Escherichia coli*, bacteria, fungi, and *Neisseria gonorrhoea*. Such probe sequences do not cross react with nucleic acids from the groups listed above, or any other bacterial species or infectious agent, under appropriate hybridization stringency conditions.

SUMMARY OF THE INVENTION

This invention discloses and claims novel probes for the detection of *Histoplasma capsulatum*. These probes are capable of distinguishing between *Histoplasma capsulatum* and its known closest phylogenetic neighbors. This probe detects unique rRNA and gene sequences encoding rRNA, and may be used in an assay for the detection and/or quantitation of *Histoplasma capsulatum*.

*Histoplasma capsulatum* is a dimorphic fungus which under different environmental conditions may exist as either the yeast or mold phase. The yeast form is unicellular and reproduces by budding on specialized media at 37° C. The mold form produces multicellular filamentous colonies that consist of cylindrical tubular structures called hyphae, and may contain microconidia and macroconidia which primarily grow under appropriate soil conditions or on specialized fungal media at 25° C. It is important to properly identify *H. capsulatum* from other fungal species in order to determine the proper treatment of any infection.

In humans, *H. capsulatum* produces the systemic fungal disease, histoplasmosis. The organism occurs throughout the world, but is most commonly found in soil from the fertile river valleys of North America and is associated with bird or bat excrement. Loyd et al., *Histoplasma capsulatum*, In *Principles and Practice of Infectious Disease*, 3rd ed. Coordinating ed., Mandell et et al., New York. pp. 1989-1999, 1990; Wheat, Diagnosis and Management of Histoplasmosis. 8 *Eur. J. Clin. Microbiol. Infect. Dis.* 480, 1989. Two additional variants of Histoplasma exist: *H. capsulatum var. duboisii* (African histoplasmosis) and *H. capsulatum var. farciminosum* (epizootic lymphangitis of horses and mules, Rippon, Histoplasmosis. In *Medical Mycology The Pathogenic Fungi and the Pathogenic Actinomycetes*. 3rd ed. Saunders Company, Chapter 15, p. 381, 1988.

Conventional laboratory identification methods used to isolate and identify *H. capsulatum* include culture of the clinical specimen at room temperature on specialized fungal media, which will isolate the slower growing *H. capsulatum* colonies from possible contaminants, such as bacteria and faster growing saprobic fungi. Growth of *H. capsulatum* to a visible colony takes from two to four weeks and may take as long as 12 weeks. Rippon, Histoplasmosis, In *Medical Mycology The Pathogenic Fungi and the Pathogenic Actinomycetes*, 3rd ed. Saunders Company. p. 381, Chapter 15, 1988; Koneman et al., Laboratory Identification of Molds, In *Practical Laboratory Mycology*, 3rd ed. Williams & Wilkins. p. 107, 1985; and McGinnis, *Histoplasma capsulatum*, In *Laboratory Handbook of Medical Mycology*, Academic Press, pp. 229-231 and 500-504, 1986. Additional growth is required before the characteristic colony morphology and microscopic sporulation pattern with tuberculate macroconidia may be observed. Approximately 10% of cultures produce only smooth walled macroconidia whereas some cultures fail to sporulate. Larsh et al., *Histoplasma capsulatum*, In *Medical Microbiology and Infectious Diseases*, eds. Davis et al., Saunders Company. pp. 654-658). Many species of fungi other than *H. capsulatum* produce similar colony and sporulation characteristics. These species include *Blas-*

*tomyces dermatitidis,* Chrysosporium sp., and Sepedonium sp. Therefore, additional testing is necessary to definitively identify the organism. One method to convert the mycelial colony to the yeast phase is by subculturing the organism onto highly enriched cysteine-containing media and incubating at 35°-37° C. However, conversion to the yeast phase is often difficult and may require several additional subcultures at three-day intervals. Immunological identification of the exoantigen may be used to further differentiate *H. capsulatum* from other fungi. Standard et al., Specific Immunological Test for the Rapid Identification of Members of the Genus Histoplasma, 3 *J. Clin. Microbio.* 191, 1980; and DeSalvo et al., Evaluation of the Exoantigen Test for Identification of Histoplasma Species and *Coccidioides immitis* Cultures. 11 *J. Clin. Microbio.* 238, 1980). The present invention provides a faster and easier method for specifically identifying *Histoplasma capsulatum.*

Thus, in a first aspect, the invention features a hybridization assay probe able to distinguish *Histoplasma capsulatum* from other closely related species of fungus.

In preferred embodiments, the probe is complementary to rRNA or rDNA, e.g., a variable region of rRNA; at least 50% of the nucleotides in the oligonucleotide probe are able to hybridize to a contiguous series of bases in at least one variable region of ribosomal nucleic acid in *Histoplasma capsulatum;* the probe is a nucleotide polymer able to hybridize to the rRNA of the species *Histoplasma capsulatum* in the region corresponding to bases 172-193 of *Saccharomyces cerevisiae* 18S rRNA, or a nucleotide polymer complementary thereto, and the oligonucleotide comprises, consists essentially of, or consists of the sequence (SEQ. ID. NO.: 1) CGAAGTCGAGGCTTTCAGCATG or oligonucleotides complementary thereto with or without a helper probe, as discussed below.

By "consists essentially of" is meant that the probe is provided as a purified nucleic acid which hybridizes under stringent hybridizing conditions with the desired organism and not with other related organisms. Such a probe may be linked to other nucleic acids which do not affect such hybridization. Generally, it is preferred that the probe be of between 15 and 100 (most preferably between 20 and 50) bases in size. It may, however, be provided in a vector.

In related aspects, the invention features a nucleotide polymer able to hybridize to the above oligonucleotide, a nucleic acid hybrid formed with the above oligonucleotides, and a nucleic acid sequence substantially complementary thereto.

The probes of this invention offer a rapid, non-subjective method of identification and quantitation of a fungal colony for the presence of specific rRNA sequences unique to all strains of *Histoplasma capsulatum.*

Other features and advantages of the invention will be apparent from the following description of the preferred embodiments thereof, and from the claims.

DESCRIPTION OF THE PREFERRED EMBODIMENT

Probes

I have discovered DNA probes complementary to a particular rRNA sequence obtained from *Histoplasma capsulatum.* Furthermore, I have successfully used those probes in a specific assay for the detection of *Histoplasma capsulatum,* distinguishing *H. capsulatum* from its known, and presumably, most closely related taxonomic or phylogenetic neighbors.

With the exception of viruses, all prokaryotic organisms contain rRNA genes encoding 5S rRNA, 16S rRNA and a larger rRNA molecule known as 23S rRNA. In the eukaryotes these rRNA molecules are the 5S rRNA, 18S rRNA and 28S rRNA and are substantially similar to the prokaryotic molecules. Using methods known to those skilled in the art, I have identified variable regions of rRNA sequences from the 18S rRNA of *Histoplasma capsulatum.* Other such sequences can be identified using equivalent techniques. These methods partially or fully sequencing the rRNA of *Histoplasma capsulatum* and closely related phylogenetic neighbors, aligning the sequences to reveal areas of maximum homology, and examining the alignment for regions with sequence variation. The examples provided below are thus not limiting in this invention.

With respect to sequencing, complementary oligonucleotide primers of about 10-100 bases in length were hybridized to conserved regions in purified rRNA that are specific to the 5S, 16S, or 23S subunits and extended with the enzyme reverse transcriptase. Chemical degradation or dideoxynucleotide-terminated sequencing reactions can be used to determine the nucleotide sequence of the extended product. Lane et al., 82 *Proc. Nat'l Acad. Sci. USA* 6955-6959, 1985. In a less preferred method, genomic ribosomal RNA sequences may also be determined by standard procedure.

It is not always necessary to determine the entire nucleic acid sequence in order to obtain a probe sequence. Extension from any single oligonucleotide primer can yield up to 300-400 bases of sequence. When a single primer is used to partially sequences the rRNA of the target organism and organisms closely related to the target, an alignment can be made as outlined below. If a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

After sequencing, the sequences are aligned to maximize homology. The rRNA molecule has a close relationship of secondary structure to function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be aligned based on the conserved primary sequence and also on the conserved secondary structure elements. Once sequences are aligned it is possible to find the regions in which the primary sequence is variable.

I have identified variable regions by comparative analysis of rRNA sequences both published in the literature and sequences which I have determined. Computers and computer programs which may be used or adapted for the purposes herein disclosed are commercially available. Since the sequence evolution at each of the variable regions (for example, spanning a minimum of 10 nucleotides) is, for the most part, divergent, not convergent, I can confidently design probes based on a few rRNA sequences which differ between the target organism and its phylogenetically closest relatives. I have seen sufficient variation between the target organism and the closest phylogenetic relative found in the same sample to design the probe of interest.

I have identified the following useful guidelines for designing probes with desired characteristics. Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe:target nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and %G and %C result in a Tm about 2°–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strength of the reaction mixture increases, and that the thermal stability of hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

Second, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe:nontarget hybrids. In designing probes, the differences in these Tm values should be as large as possible (e.g., at least 2° C. and preferably 5° C.).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-complementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intramolecular hybrids. By designing a probe so that a substantial portion of the sequence of interest is single stranded the rate and extent of hybridization may be greatly increased. If the target is the genomic sequence corresponding to the rRNA then it will naturally occur in a double stranded form, this is also the case with the product of the polymerase chain reaction (PCR). These double stranded targets are naturally inhibitory to hybridization with a probe. Finally, there can be intramolecular and intermolecular hybrids formed within a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone et al., 12 *Nucleic Acids Research* 4051, 1984. Other well-known methods for construction of synthetic oligonucleotides may, of course, be employed. Sambrook et al., 2 *Molecular Cloning* 11 (2d ed. 1989).

Once synthesized, selected oligonucleotide probes may also be labelled by any of several well known methods. Sambrook et al., 2 *Molecular Cloning* 11 (2d ed. 1989). Useful labels include radioisotopes as well as non-radioactive reporting groups. Isotopic labels include $^3H$, $^{35}S$, $^{32}P$, $^{125}I$, $^{57}Co$ and $^{14}C$. Most methods of isotopic labelling involve the use of enzymes and include the known methods of nick translation, end labelling, second strand synthesis, and reverse transcription. When using radio-labelled probes, hybridization can be detected by autoradiography, scintillation counting, or gamma counting. The detection method selected will depend upon the hybridization conditions and the particular radio isotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. I currently prefer to use acridinium esters.

Following synthesis and purification of a particular oligonucleotide sequence, several procedures may be utilized to determine the acceptability of the final product. The first is polyacrylamide gel electrophoresis, which is used to determine size. Sambrook et al., 2 *Molecular Cloning*, 11.51 (2d ed. 1989). Such procedures are known in the art. In addition to polyacrylamide gel electrophoresis, High Pressure Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., patent application Ser. No. 613,603 filed Nov. 8, 1990, entitled "Homogeneous Protection Assay" assigned to Gen-Probe Incorporated, Mar. 6, 1992, Reel/Frame 6057/0433-34, also published under European Patent Application Publication Number 0 309 230, Mar. 29, 1989 (hereby incorporated by reference herein).

For Tm measurement using a Hybridization Protection Assay (HPA) the following technique is used. A probe:target hybrid is formed in target excess in a lithium succinate buffered solution containing lithium lauryl sulfate. Aliquots of this hybrid are diluted in the hybridization buffer and incubated for five minutes at various temperatures starting below that of the anticipated Tm (typically 55° C.) and increasing in 2-5 degree increments. This solution is then diluted with a mildly alkaline borate buffer and incubated at a lower temperature (for example 50° C.) for ten minutes. Under these conditions the acridinium ester attached to a single stranded probe is hydrolyzed while that attached to hybridized probe is relatively protected from hydrolysis. The amount of chemiluminescence remaining is proportional to the amount of hybrid, and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which affect relative hybrid stability during thermal denaturation. 2 J. Sambrook, E. F. Fritsch and T. Maniatis, *Molecular Cloning*, 9.51 (2d ed. 1989).

Rate of hybridization may be measured by determining the $C_0t_{\frac{1}{2}}$. The rate at which a probe hybridizes to its target is a measure of the thermal stability of the target secondary structure in the probe region. The standard measurement of hybridization rate is the $C_0t_{\frac{1}{2}}$ which is measured as moles of nucleotide per liter times seconds. Thus, it is the concentration of probe times the time at which 50% of maximal hybridization occurs at that concentration. This value is determined by hybridizing various amounts of probe to a constant amount of target for a fixed time. For example, 0.05 pmol of target is incubated with 0.012, 0.025, 0.05, 0.1 and 0.2 pmol of probe for 30 minutes. The amount of hybrid after 30 minutes is measured by HPA as described above. The signal is then plotted as a log of the percent of maximum Relative Light Units (RLU) (from the highest probe concentration) versus probe concentration (moles of nucleotide per liter). RLU are a measurement of the quantity of photons emitted by the labelled-probe measured by the luminometer. The $C_0t_{\frac{1}{2}}$ is found graphically from the concentration corresponding to 50% of maximum hybridization multiplied by the hybridization time in seconds. These values range from $9.0 \times 10^{-6}$ to $9 \times 10^{-5}$ with the preferred values being less than $3.5 \times 10^{-5}$.

As described by Kohne and Kacian (U.S. Ser. No. 816,711, entitled "Accelerated Nucleic Acid Reassociation Method," filed Jan. 7, 1986 abandoned in favor of U.S. application Ser. No. 644,879, filed Jan. 23, 1991, allowed Feb. 7, 1992, assigned to Gen-Probe Incorporated, Apr. 14, 1986, Reel/Frame 4538/0494, also published under European Patent Application Publication Number 0 229 442, Jul. 22, 1987 hereby incorporated by reference herein) other methods of nucleic acid reassociation can be used.

The following example sets forth a synthetic probe complementary to a unique rRNA sequence, or the corresponding gene, from a target organism, *Histoplasma capsulatum*, and its use in a hybridization assay.

EXAMPLE

A probe specific for *H. capsulatum* was identified by sequencing with a primer complementary to the 18S rRNA. The following sequence was characterized and shown to be specific for *Histoplasma capsulatum,* 5' CGAAGTCGAGGCTTTCAGCATG 3'. The phylogenetically near neighbors *Blastomyces dermatitidis, Cryptococcus neoformans,* and *Coccidioides immitis* were used as comparisons with the sequence of *H. capsulatum.*

This probe is 22 bases in length and hybridizes to the 18S rRNA of *H. capsulatum* corresponding to bases 172–193 of *Sacchromyces cerevisiae.* To demonstrate the reactivity and specificity of the probe for *H. capsulatum,* it was used in a hybridization assay. The probe was first synthesized with a non-nucleotide linker, then labelled with a chemiluminescent acridinium ester as described in EPO Patent Application No. PCT/US88/03361, entitled "Acridinium Ester Labeling and Purification of Nucleotide Probes, filed Oct. 5, 1988, (hereby incorporated herein by reference). The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in RLU, the quantity of photons emitted by the labelled-probe measured by the luminometer. The conditions of hybridization, hydrolysis and detection are described in Arnold et al., 35 *Clin. Chem.* 1588, 1989.

Nucleic acid hybridization was enhanced by the use of Helper Probes as disclosed in Hogan et al., U.S. Pat. No. 5,030,557, entitled "Means and Methods for Enhancing Nucleic Acid Hybridization", allowed Dec. 17, 1990, and hereby incorporated by reference herein. RNA was hybridized to a mix of the acridinium ester-labeled probe in the presence of unlabeled Helper Probes, oligonucleotides with the sequence SEQ. ID. NO.: 2: 5' TATTAGCTCTAGAATTACCACGG-GTATCCAAGTAGTAAGG 3' and SEQ. ID. NO.: 3: 5'CCCCGAAGGGCATTGGTTTTTATC-TAATAAATACACCCC 3'.

In the following experiment, RNA released from one colony or $>10^8$ organisms was assayed. An example of such a method is provided by Murphy et al., U.S. Ser. No. 841,860, entitled "Method for Releasing RNA and DNA from Cells", filed Mar. 20, 1986, abandoned in favor of U.S. Ser. No. 298,765, filed Jan. 17, 1989, abandoned in favor of U.S. Ser. No. 711,114, filed Jun. 21, 1991, assigned to Gen-Probe Incorporated, May 23, 1986, Reel/Frame 4566/0901, also published under European Patent Application Publication Number 0 228 618, Feb. 11, 1988 hereby incorporated by reference herein. RLU values greater than 30,000 RLU are a positive reaction; less than 30,000 is a negative reaction. The following data show that the probe did not cross react with organisms from a wide phylogenetic cross section. Thus, the probe is useful for specific detection of *Histoplasma capsulatum.*

| ORGANISM (mating or serotype) | F/Y | ATCC NO. | RLU |
|---|---|---|---|
| *Acremonium strictum* | | 10141 | 3174 |
| *Ajellomyces* (Histoplasma) *capsulata* (−) | F | 22635 | 600653 |
| *Ajellomyces* (Histoplasma) *capsulata* (+) | F | 22636 | 507781 |
| *Ajellomyces* (Blastomyces) *dermatitidis* (a) | F | 18188 | 5439 |
| *Ajellomyces* (Blastomyces) *dermatitidis* (A) | F | 18187 | 3406 |
| *Ajellomyces* (Histoplasma) *capsulata* (−) | Y | 22635 | 468485 |
| *Ajellomyces* (Histoplasma) *capsulata* (+) | Y | 22636 | 537159 |
| *Ajellomyces* (Blastomyces) *dermatitidis* (a) | Y | 18188 | 3293 |
| *Ajellomyces* (Blastomyces) *dermatitidis* (A) | Y | 18187 | 2250 |
| *Apiotrichum* (Candida) *humicola* | | 14438 | 1669 |
| *Arachniotus flavoluteus* | | 28364 | 2295 |
| *Arthroderma tuberculatum* | | 26700 | 2534 |
| *Aspergillus flavus* | | 10124 | 3169 |
| *Aspergillus fumigatus* | | 36607 | 2216 |
| *Aspergillus fumigatus* var. *ellipticus* | | 16093 | 5541 |
| *Aspergillus nidulans* | | 10074 | 13190 |
| *Aspergillus niger* | | 16888 | 20042 |
| *Aspergillus terreus* | | 7860 | 4455 |
| *Aureobasidium pullulans* | | 16622 | 2508 |
| *Auxarthron thaxteri* | | 15598 | 2139 |
| *Blastomyces dermatitidis* | F | 26199 | 1164 |
| *Blastomyces dermatitidis* (attenuated strain) | F | 60916 | 6555 |
| *Blastomyces dermatitidis* | Y | 26199 | 2826 |
| *Blastomyces dermatitidis* (attenuated strain) | Y | 60916 | 4801 |
| *Blastoschizomyces* (Trichosporon) *capitatus* | | 28576 | 1463 |

-continued

| ORGANISM (mating or serotype) | F/Y | ATCC NO. | RLU |
|---|---|---|---|
| *Candida albicans* (*stellatoidia*) | | 36232 | 1733 |
| *Candida albicans* | | 24433 | 1724 |
| *Candida famata* | | 36584 | 2324 |
| *Candida glabrata* | | 48435 | 2333 |
| *Candida guilliermondii* | | 6260 | 1721 |
| *Candida kefur* | | 46764 | 1807 |
| *Candida kefyr* | | 2512 | 2386 |
| *Candida krusei* | | 14243 | 1692 |
| *Candida lambica* | | 24750 | 2005 |
| *Candida lustitaniae* | | 42720 | 1738 |
| *Candida parapsilosis* | | 34136 | 1906 |
| *Candida rugosa* | | 58964 | 2029 |
| *Candida tropicalis* | | 13803 | 1777 |
| *Candida tropicalis* (*paratropicalis*) | | 34139 | 1774 |
| *Chaetomium globosum* | | 44699 | 2799 |
| *Chionosphaera apobasidialis* | | 52639 | 1556 |
| *Chrysosporium keratinophilum* | | 14803 | 1825 |
| *Cladosporium herbarum* | | 28987 | 6324 |
| *Coccidioides immitis* | | 28868 | 3239 |
| *Corynascus sepedonium* | | 42828 | 2404 |
| *Cryptococcus albidus* var. *albidus* | | 10666 | 6293 |
| *Crytococcus albidus* var *diffluens* | | 34141 | 3011 |
| *Cryptococcus gastricus* | | 24225 | 2815 |
| *Cryptococcus laurentii* | | 34142 | 1396 |
| *Cryptococcus luteolus* | | 32044 | 2712 |
| *Cryptococcus neoformans* | | 14116 | 2709 |
| *Cryptococcus terreus* | | 11799 | 3892 |
| *Cryptococcus uniguttulatus* | | 34143 | 1971 |
| *Epidermophyton floccosum* | | 50266 | 4929 |
| *Filobasidiella* (Cryptococcus) *neoformans* (sero. A) | | 6352 | 2101 |
| *Filobasidiella* (Cryptococcus) *neoformans* (sero. C) | | 32608 | 2401 |
| *Filobasidiella* (Cryptococcus) *neoformans* (sero. C) | | 32608 | 1950 |
| *Filobasidiella* (Cryptococcus) *neoformans* (sero. D) | | 28958 | 4263 |
| *Filobasidiella* (Cryptococcus) *neoformans* (sero. D) | | 28958 | 3166 |
| *Filobasidiella* (Cryptococcus) *neoformans* (sero. B) | | 32269 | 1944 |
| *Filobasidium capsuligenum* | | 22179 | 2244 |
| *Fusarium oxysporum* | | 48112 | 2216 |
| *Geotrichum candidum* | | 34614 | 2145 |
| *Gymnoascus dugwayensis* | | 18899 | 2789 |
| *Hanseniaspora guillermondii* | | 10630 | 3447 |
| *Hansenula anomala* | | 8168 | 2807 |
| *Histoplasma capsulatum* (atenuated Downs strain) | F | 38904 | 660104 |
| *Histoplasma capsulatum* | F | 11407 | 518019 |
| *Histoplasma capsulatum* var. *duboisii* | F | 32281 | 641701 |
| *Histoplasma capsulatum* var. *farciminosum* | F | 58332 | 554211 |
| *Histoplasma capsulatum* (attenuated Downs strain) | Y | 38904 | 579441 |
| *Histoplasma capsulatum* | Y | 11407 | 494979 |
| *Histoplasma capsulatum* var. *duboisii* | Y | 32281 | 445182 |
| *Histoplasma capsulatum* var. *farciminosum* | Y | 58332 | 407623 |
| *Malbranchea albolutea* | | 34522 | 3629 |
| *Malbranchea arcuata* | | 34523 | 2563 |
| *Microsporum gypseum* | | 24102 | 2047 |
| *Myxotrichum deflexum* | | 15686 | 2185 |
| *Oidiodendron echinulatum* | | 16287 | 3162 |
| *Penicillium notatum* | | 11625 | 3729 |
| *Prototheca wickerhamii* | | 16529 | 3299 |
| *Pseudallescheria boydii* (*Scedosporium apiospermum*) | | 58034 | 5114 |
| *Rhizopus oligosporus* | | 22959 | 2578 |
| *Rhodotorula glutinis* | | 32765 | 1896 |
| *Rhodotorula minuta* | | 60108 | 3566 |
| *Rhodotorula rubra* | | 9449 | 5428 |
| *Saccharomyces cerevisiae* | | 18824 | 2331 |
| *Scopulariopsis acremonium* | | 58636 | 2664 |
| *Sepedonium chrysospermum* | | 16084 | 2875 |
| *Sporobolomyces salmonicolor* | | 32311 | 2227 |
| *Sporothrix schenckii* | F | 14284 | 2906 |
| *Torulopsis glabrata* | | 2001 | 2164 |
| *Trichophyton mentagrophytes* | | 18748 | 9089 |

-continued

| ORGANISM (mating or serotype) | F/Y | ATCC NO. | RLU |
|---|---|---|---|
| Trichosporon beigelii | | 28592 | 4181 |
| Uncinocarpus reesii | | 34533 | 2580 |

*Y = yeast phase,
F = filamentous phase

The above data confirm that the novel probes herein disclosed and claimed are capable of distinguishing Histoplasma capsulatum from its known nearest phylogenetic neighbors.

Other embodiments are within the following claims.

I claim:

1. A nucleic acid hybridization assay probe having sufficient complementarity to the rRNA or rDNA sequences of Histoplasma capsulatum, or to sequences complementary thereto, able to distinguish, under hybridization conditions, Histoplasma capsulatum from Blastomyces dermatitidis.

2. The probe of claim 1, wherein said probe is complementary to rRNA or rDNA.

3. The probe of claim 1 or 2, wherein said nucleic acid is complementary to 5S, 18S, or 28S rRNA, or corresponding genomic DNA.

4. A nucleotide polymer consisting essentially of the sequence SEQ. ID NO. 1 CGAAGTCGAGGCTTTCAGCATG, or an oligonucleotide complementary thereto.

5. A probe mix consisting essentially of the sequence CGAAGTCGAGGCTTTCAGCATG and a nucleic acid helper probe.

6. The probe mix of claim 5, wherein said helper probe is an oligonucleotide having the sequence CCCCGAAGGGCATTGGTTTTTTATC-TAATAAATACACCCC or TATTAGCT-CTAGAATTACCACGGGTATCCAAGTAG-TAAGG.

7. The probe of claim 1, wherein said probe distinguishes Histoplasma capsulatum from Blastomyces dermatitidis, Arthroaerma tuberculatum, Chrysosporium keratinophilum, Coccidioides immitis, Corynascus sepedonium, Sepedonium chrysospermum, and Scopulariopsis acremonium.

8. A nucleic acid hybrid formed between an oligonucleotide, consisting essentially of the sequence CGAAGTCGAGGCTTTCAGCATG and a nucleotide polymer sufficiently complementary thereto to allow hybridization under stringent hybridization conditions.

9. An oligonucleotide consisting essentially of between 10 and 100 nucleotides, inclusive, able to form a hybrid at 60° C. with a nucleotide polymer having a nucleotide base sequence selected from a group consisting of 5' CGAAGTCGAGGCTTTCAGCATG, 5' CATGCTGAAAGCCTCGACTTCG, 5' CAUG- CUGAAAGCCUCGACUUCG, or 5' CGAAGUC-GAGGCUUUCAGCAUG.

10. The oligonucleotide of claim 9, wherein said oligonucleotide consists essentially of between 15 to 100 bases.

11. The oligonucleotide of claim 9, wherein said oligonucleotide consists essentially of between 10 to 50 bases.

12. The oligonucleotide of claim 9, wherein said oligonucleotide consists essentially of between 20 to 50 bases.

13. A method for distinguishing *Histoplasma capsulatum* from *Blastomyces dermatitidis, Arthroderma tuberculatum, Chrysosporium keratinophilum, Coccidioides immitis, Corynascus sepedonium, Scopulariopsis acremonium,* and *Sepedonium chrysospermum,* comprising the step of hybridizing a nucleic acid hybridization assay probe which is able to hybridize to *Histoplasma capsulatum* rRNA and not to rRNA from said other species of fungi.

14. The hybridization assay probe of claim 1, wherein said probe consists essentially of an oligonucleotide having sufficient complementarity to a region of ribosomal nucleic acid which varies between fungi to hybridize to *Histoplasma capsulatum* and not to *Blastomyces dermatitidis, Arthroderma tuberculatum, Chrysosporium keratinophilum, Coccidioides immitis, Corynascus sepedonium, Scopulariopsis acremonium,* and *Sepedonium chrysospermum.*

15. The probe of claim 7, wherein said probe is complementary to rRNA or rDNA.

* * * * *

UNITED STATES PATENT AND TRADEMARK OFFICE
CERTIFICATE OF CORRECTION

PATENT NO. : 5,352,579
DATED : October 4, 1994
INVENTOR(S) : Curt L. Milliman

It is certified that error appears in the above-identified patent and that said Letters Patent is hereby corrected as shown below:

On the title page,
    Assignee: [Gen-Probe, Inc.] <u>Gen-Probe Incorporated</u>

Signed and Sealed this

Thirteenth Day of June, 1995

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
      ( A ) LENGTH: 22
      ( B ) TYPE: nucleic acid
      ( C ) STRANDEDNESS: single
      ( D ) TOPOLOGY: linear ( i i ) SEQUENCE DESCRIPTION: SEQ ID NO: 1:

CGAAGTCGAG GCTTTCAGCA TG                           2 2

( 2 ) INFORMATION FOR SEQ ID NO: 2:

( i ) SEQUENCE CHARACTERISTICS:
      ( A ) LENGTH: 40
      ( B ) TYPE: nucleic acid
      ( C ) STRANDEDNESS: single
      ( D ) TOPOLOGY: linear ( i i ) SEQUENCE DESCRIPTION: SEQ ID NO: 2:

TATTAGCTCT AGAATTACCA CGGGTATCCA AGTAGTAAGG         4 0

( 2 ) INFORMATION FOR SEQ ID NO: 3:

( i ) SEQUENCE CHARACTERISTICS:
      ( A ) LENGTH: 40
      ( B ) TYPE: nucleic acid
      ( C ) STRANDEDNESS: single
      ( D ) TOPOLOGY: linear ( i i ) SEQUENCE DESCRIPTION: SEQ ID NO: 3:

CCCCGAAGGG CATTGGTTTT TTATCTAATA AATACACCCC         4 0